US006939556B2

(12) United States Patent
Lautenbach

(10) Patent No.: US 6,939,556 B2
(45) Date of Patent: Sep. 6, 2005

(54) MINIMALLY COMPLIANT, VOLUME EFFICIENT PISTON FOR OSMOTIC DRUG DELIVERY SYSTEMS

(75) Inventor: Scott D. Lautenbach, San Mateo, CA (US)

(73) Assignee: Alza Corporation, Mountain View, CA (US)

( * ) Notice: Subject to any disclaimer, the term of this patent is extended or adjusted under 35 U.S.C. 154(b) by 150 days.

(21) Appl. No.: 10/606,407

(22) Filed: Jun. 25, 2003

(65) Prior Publication Data

US 2004/0019345 A1 Jan. 29, 2004

Related U.S. Application Data

(60) Provisional application No. 60/392,004, filed on Jun. 26, 2002.

(51) Int. Cl.[7] .............................. A61F 2/00; A61K 9/22
(52) U.S. Cl. ..................................... 424/424; 604/892.1
(58) Field of Search ........................ 604/892.1, 890.1; 424/438, 424, 452, 423, 433, 436, 422, 425

(56) References Cited

U.S. PATENT DOCUMENTS

| 4,753,651 A | 6/1988 | Eckenhoff .................... 424/449 |
| 4,765,989 A | 8/1988 | Wong et al. .................. 424/473 |
| 4,874,388 A | 10/1989 | Wong et al. ............... 604/891.1 |
| 4,969,884 A | 11/1990 | Yum ........................ 604/892.1 |
| 5,030,216 A | 7/1991 | Theeuwes ................. 604/892.1 |
| 5,034,229 A | 7/1991 | Margruder et al. .......... 424/422 |
| 5,137,727 A | 8/1992 | Eckenhoff .................... 424/422 |
| 5,180,591 A | 1/1993 | Margruder et al. .......... 424/473 |
| 5,209,746 A | 5/1993 | Balaban et al. ........... 604/892.1 |
| 5,221,278 A | 6/1993 | Linkwitz et al. .......... 604/890.1 |
| 5,234,424 A | 8/1993 | Yum et al. ................ 604/892.1 |
| 5,234,692 A | 8/1993 | Margruder et al. .......... 424/473 |
| 5,308,348 A | 5/1994 | Balaban et al. ........... 604/892.1 |
| 5,318,558 A | 6/1994 | Linkwitz et al. .......... 604/892.1 |

(Continued)

FOREIGN PATENT DOCUMENTS

WO         99 33446         7/1999

OTHER PUBLICATIONS

International Search Report dated Nov. 4, 2003 for corresponding Appln. No. PCT/US03/21361.

*Primary Examiner*—Sharon Kennedy
(74) *Attorney, Agent, or Firm*—TraskBritt

(57) ABSTRACT

An osmotic pump having a minimally compliant, volume-efficient piston positioned within a capsule is provided. The capsule has an interior surface, a beneficial agent, and an osmotic agent. The piston is movable with respect to an interior surface of the capsule, and defines a movable seal with the interior surface of the capsule. The movable seal separates the osmotic agent from the beneficial agent. The piston has a length-to-total-diameter ratio of about 1.1:1 and a core-diameter-to-total-diameter ratio of about 0.9:1. The piston enables greater beneficial agent and/or osmotic agent payload without increasing the size of the capsule. The osmotic agent imbibes liquid from a surrounding environment through a semipermeable body to cause the piston to move and, in turn, cause delivery of the beneficial agent from the capsule.

16 Claims, 1 Drawing Sheet

U.S. PATENT DOCUMENTS

| | | | |
|---|---|---|---|
| 5,324,280 A | 6/1994 | Wong et al. | 604/892.1 |
| 5,456,679 A | 10/1995 | Balaban et al. | 604/892.1 |
| 5,531,736 A | 7/1996 | Wong et al. | 604/892.1 |
| 5,540,665 A | 7/1996 | Mercado et al. | 604/145 |
| 5,690,952 A | 11/1997 | Mragruder et al. | 424/423 |
| 5,728,088 A | 3/1998 | Margruder et al. | 604/892.1 |
| 5,728,396 A | 3/1998 | Peery et al. | 424/422 |
| 5,795,591 A | 8/1998 | Lee et al. | 424/473 |
| 5,861,166 A | 1/1999 | Eckenhoff | 424/422 |
| 5,871,770 A | 2/1999 | Margruder et al. | 424/423 |
| 5,985,305 A | 11/1999 | Peery et al. | 424/422 |
| 5,997,527 A | 12/1999 | Gumucio et al. | 604/892.1 |
| 6,132,420 A | 10/2000 | Dionne et al. | 604/892.1 |
| 6,156,331 A | 12/2000 | Peery et al. | 424/422 |
| 6,217,906 B1 | 4/2001 | Gumucio et al. | 424/473 |
| 6,261,584 B1 | 7/2001 | Peery et al. | 424/422 |
| 6,287,295 B1 * | 9/2001 | Chen et al. | 604/892.1 |
| 6,395,292 B2 | 5/2002 | Peery et al. | 424/422 |
| 2001/0036472 A1 | 11/2001 | Wong et al. | 424/456 |
| 2003/0114837 A1 * | 6/2003 | Peterson et al. | 604/892.1 |

* cited by examiner

MINIMALLY COMPLIANT, VOLUME EFFICIENT PISTON FOR OSMOTIC DRUG DELIVERY SYSTEMS

This application claims the priority of provisional application Ser. No. 60/392,004, filed Jun. 26, 2002, which is incorporated herein by reference.

FIELD OF THE INVENTION

The present invention relates to osmotic systems for delivering beneficial agents. More particularly, the present invention relates to an osmotic pump having a minimally compliant, volume-efficient piston.

DESCRIPTION OF THE RELATED ART

Controlled delivery of beneficial agents, such as drugs, in the medical and veterinary fields, has been accomplished by a variety of methods. One method for controlled prolonged delivery of beneficial agents involves the use of osmotic delivery systems. These devices can be implanted to release beneficial agents in a controlled manner over a preselected time or administration period. In general, osmotic delivery systems operate by imbibing liquid from the outside environment and releasing corresponding amounts of the beneficial agent.

A known osmotic delivery system, commonly referred to as an "osmotic pump," generally includes some type of capsule or enclosure having a semipermeable portion that may selectively pass water into an interior of the capsule that contains a water-attracting osmotic agent. Often, the walls of the capsule included in known osmotic pumps are substantially impermeable to items within and outside the capsule and the semipermeable portion is formed as a plug of semipermeable material. The difference in osmolarity between the water-attracting agent and the exterior of the capsule causes water to pass through the semipermeable portion of the capsule, which, in turn, causes the beneficial agent to be delivered from the capsule through the delivery port. The water-attracting agent may be the beneficial agent delivered to the patient. However, in most cases, a separate osmotic agent is used specifically for its ability to draw water into the capsule.

In some instances, a piston is required to separate the beneficial agent from the osmotic agent to prevent the osmotic agent from mixing with or contaminating the beneficial agent. Examples of systems that use a piston to separate the beneficial agent from the osmotic agent include U.S. Pat. Nos. 4,753,651; 4,874,388; 4,969,884; 5,030,216; 5,034,229; 5,137,727; 5,180,591; 5,209,746; 5,221,278; 5,234,424; 5,234,692; 5,308,348; 5,318,558; 5,456,679; 5,540,665; 5,690,952; 5,728,088; 5,728,396; 5,795,591; 5,861,166; 5,871,770; 5,985,305; 5,997,527; 6,132,420; 6,156,331; 6,217,906; 6,261,584; 6,287,295; and 6,395,292; and PCT publication WO 99/33446, the entire disclosures of each are herein incorporated by reference. Where the dimensions of the pistons included in the osmotic pumps described claimed in the cited references are described, the ratio of length-to-total-width of the piston is typically lengthen 1:0:1.However, the cited references do not provide details regarding the ratio of the core of the pistons to the total diameter of the pistons used in these systems described therein. The structure of the capsules described in the cited references is such that the capsule does not expand significantly when the osmotic agent takes in water and expands. As the osmotic agent included in the systems described in the cited references expands, pressure causes the piston to move and the beneficial agent to be discharged through the delivery orifice at the same rate as the liquid, which is typically water, enters the osmotic agent by osmosis. The osmotic pumps described in the cited references may be designed to deliver a beneficial agent at a controlled constant rate, a varying rate, or in a pulsatile manner.

A piston included in an osmotic pump necessarily occupies space within the device. Hence, if a piston is needed to separate the beneficial agent and the osmotic agent, and the size of the capsule included in an osmotic pump is not changed, the amount of beneficial agent or osmotic agent that can be held within the capsule decreases relative to an osmotic pump that has the same size capsule but lacks a piston. Such a decrease in capacity may work to reduce the net amount of beneficial agent that can be delivered from the osmotic pump over a sustained period of time. Alternatively, the decrease in loading capacity caused by the inclusion of a piston may result in a reduction of the amount of osmotic agent included in the osmotic pump, which, in turn, can work to reduce the period of time over which the osmotic pump can achieve a desired release rate or release rate profile of beneficial agent. Therefore, the need to include a piston in an osmotic pump may result in the simultaneous need to increase the size or volume of the capsule included in the osmotic pump in order to achieve delivery of beneficial agent at a desired release rate or release rate profile over a chosen period of time.

Though simply increasing the size or volume of the capsule included in an osmotic pump to accommodate the extra volume occupied by the piston may appear to be a simple solution, such an approach is not without drawbacks. For instance, many osmotic pumps are destined for implantation in humans or animals, and it is highly desirable to decrease the size of such pumps as much as possible, while providing a device capable of delivering the chosen beneficial agent at a desired rate over a prolonged period of time. Additionally, it would be desirable to use one capsule size for multiple osmotic pump applications. With such a goal in mind, increasing the size of the capsule for those applications requiring a piston may be inexpedient, as it could require differently sized capsules to achieve delivery of the same amount of beneficial agent depending on whether or not the osmotic pump utilized a piston.

It would be an improvement in the art, therefore, to provide an osmotic pump that includes a piston, wherein the piston provides increased space efficiency. Ideally, the piston design of such a device would allow the fabrication of an osmotic pump that includes a piston but can accommodate relatively more osmotic agent or more beneficial agent when compared to an osmotic pump of the same size and volume that incorporates a piston according to previous designs. By allowing an osmotic pump of given dimensions that includes a piston to accommodate relatively more beneficial agent or relatively more osmotic agent, such a device would work to increase the amount of beneficial agent that can be delivered from the device, the period of time over which the beneficial agent is released, or both.

SUMMARY OF THE INVENTION

Generally speaking, the present invention provides an osmotic pump that includes a piston separating the osmotic agent and beneficial agent included in the pump. The piston included in an osmotic pump of the present invention works to provide improved space efficiency relative to previous designs.

In one aspect, the present invention includes an osmotic pump that includes a capsule. The capsule is impermeable to liquids and has an interior for holding a beneficial agent. The interior of the capsule has an interior surface. An osmotic agent is located in the interior of the capsule. A semipermeable body is in liquid communication with the capsule and permits liquid to permeate through the semipermeable body to the osmotic agent. A piston is located within the interior of the liquid impermeable capsule. The piston is movable with respect to the interior surface of the capsule and defines a movable seal with the interior surface of the capsule. The movable seal defined by the piston separates the osmotic agent from the beneficial agent. The piston has at least one annular ring or rib that forms a seal between the piston and the interior surface of the capsule. The osmotic agent is located between the piston and the semipermeable body. The osmotic agent imbibes liquid from a surrounding environment through the semipermeable body to cause the piston to move and in turn cause delivery of the beneficial agent from the capsule.

In another aspect, the present invention provides an osmotic pump that includes a piston, wherein the piston has a length to total width or diameter of about 1.1:1. This ratio allows for an increase in beneficial agent and/or osmotic agent payload without increasing the size of the capsule.

In yet another aspect, the present invention includes a capsule and a piston having one or more annular rings or ribs ("ring," "rings," "rib," and "ribs" are used interchangeably unless otherwise noted), wherein the one or more annular rings provided on the piston have a shallow profile that works to reduce the space for air entrapment during insertion of the piston into the capsule. Such a ring profile is obtained by the piston having a ratio of core-diameter-to-total-width-or-diameter of about 0.9:1. Where the osmotic pump of the present invention includes a piston having rings or ribs characterized by a shallow profile, the rings or ribs may be designed to reduce the springiness and linear compressibility of the piston.

Other objects, advantages and features associated with the present invention will become readily apparent to those skilled in the art from the following detailed description. As will be realized, the invention is capable of modification in various obvious aspects, all without departing from the invention. Accordingly, the drawings and the description are to be regarded as illustrative in nature and not limitative.

BRIEF DESCRIPTION OF THE DRAWINGS

The invention will be described in greater detail with reference to the accompanying drawings in which like elements bear like reference numerals, and wherein.

DETAILED DESCRIPTION OF THE INVENTION

The present invention provides a device for the delivery of a beneficial agent to a fluid environment of use that includes a volume-efficient piston that minimizes leakage between the beneficial agent and the osmotic agent and enables larger beneficial agent and/or osmotic agent payloads.

Definitions

The term "beneficial agent" is intended to include beneficial agent(s), optionally, in combination with pharmaceutically acceptable carriers and, optionally, additional ingredients such as antioxidants, stabilizing agents, etc.

Use of the terms "time to start-up of delivery" is intended to mean the time from insertion into the fluid environment of use until the beneficial agent is actually delivered at a rate not less than approximately 70% of the intended steady-state rate.

The term "impermeable" means that the material is sufficiently impermeable to environmental fluids, as well as ingredients contained within the dispensing device, such that the migration of such materials into or out of the device through the impermeable device is so low as to have substantially no adverse impact on the function of the device during the delivery period.

The term "semipermeable" means that the material is permeable to external fluids but substantially impermeable to other ingredients contained within the dispensing device and the environment of use.

The beneficial agent delivery devices of the present invention find use where the prolonged and controlled delivery of a beneficial agent is desired. In many cases, the beneficial agent is susceptible to degradation if exposed to the environment of use prior to delivery. The devices protect the agent from such exposure.

Figure 1:
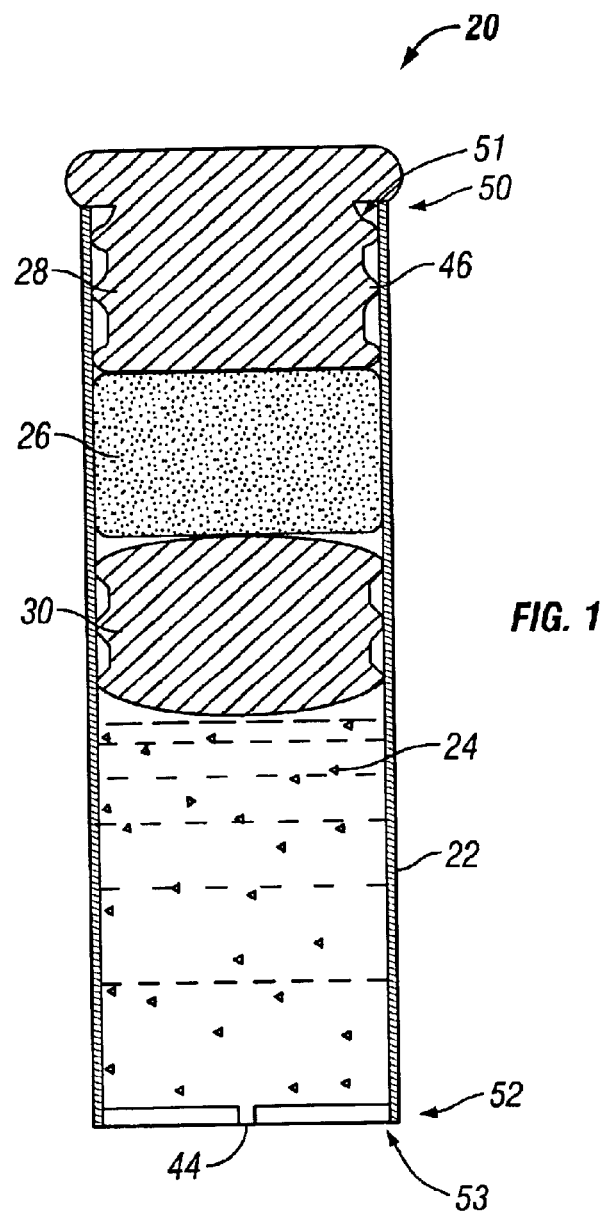
FIG. 1 is a cross-sectional view of an osmotic pump according to the present invention.

As shown in FIG. 1, the present invention relates to an osmotic pump 20 for delivering a beneficial agent 24. The osmotic pump 20 includes a minimally compliant, volume-efficient piston 30. The osmotic pump 20 also includes a capsule 22 that encloses the piston 30 and an osmotic agent 26. The piston 30 is movable within the capsule 22 and defines a movable seal that substantially prevents the osmotic agent 26 and the beneficial agent 24 from adversely affecting one another. The piston 30 includes at least one annular ring or rib, such that when the piston is inserted into the capsule 22, the ring or rib forms, along with the core of the piston, a fluid seal with the interior surface of the capsule 22. A semipermeable body 28 is in liquid communication with the osmotic agent 26 and permits liquid to permeate through the semipermeable body 28 to the osmotic agent 26. The osmotic agent 26 imbibes the liquid from a surrounding environment and causes the piston 30 to move, which, in turn, causes the beneficial agent 24 to be released from the osmotic pump 20.

The configuration of the osmotic pump 20, according to the present invention illustrated in FIG. 1, is one example of an osmotic delivery device and is not to be construed as limiting the present invention. The present invention is generally applicable to all osmotic delivery devices having any number of shapes, and to all such devices administered in any variety of methods, such as oral, ruminal, and implantable osmotic delivery techniques.

The capsule 22 of the osmotic pump 20 encloses or contains the osmotic agent 26 and the piston body 32. The capsule 22 includes a tubular or elongated and substantially cylindrical capsule 22 illustrated in FIG. 1. The capsule 22 has a first opening 51 at a first end 50 and a second opening 53 at a second end 52 opposite the first end 50. The capsule 22 also includes the semipermeable body 28 that obstructs, blocks, closes off, or plugs the first opening 51 in the capsule 22 to enclose the osmotic agent 26 and piston body 32. Thus, the first opening 51 receives the semipermeable body 28.

The capsule 22 also includes a delivery port 44 located at the second end 52 of the capsule 22. As beneficial agent 24 is delivered from the osmotic pump 20, the beneficial agent is expelled through the delivery port 44. The delivery port 44 may be an orifice formed by conventional techniques.

Included among these methods are mechanical drilling, laser drilling, and molding. The capsule 22 will contain at least one such delivery port 44 and, in most configurations, one delivery port 44 will suffice. However, two or more delivery ports 44 may be present without departing from the present invention. The delivery port 44 may be formed in the capsule 22 itself, or may be formed in a separate and distinct plug-like member for insertion into the second opening 53 of the capsule 22. The delivery port 44 can be a slit orifice, such as that disclosed in U.S. Pat. No. 5,997,527, the entire disclosure of which is hereby incorporated by reference, or a spiral orifice, such as that disclosed in U.S. Pat. No. 5,728,396, the entire disclosure of which is hereby incorporated by reference.

The delivery port 44 is made of an inert and biocompatible material selected from, but not limited to, metals including, but not limited to, titanium, stainless steel, platinum and their alloys and cobalt-chromium alloys and the like, and polymers including, but not limited to, polyethylene, polypropylene, polycarbonate and polymethylmethacrylate and the like.

The dimensions of the delivery port 44 in terms of both diameter and length will vary with the type of beneficial agent 24, the rate at which the beneficial agent is to be delivered, and the environment into which it is to be delivered. The considerations involved in determining the optimum dimensions of the delivery port 44 for any particular capsule or beneficial agent 24 are the same as those for delivery ports or orifices of capsules in the prior art, and selection of the appropriate dimensions will be readily apparent to those skilled in the art.

The capsule 22 is formed of a material that is sufficiently rigid to withstand expansion of an osmotic agent 26 without significant changes in size or shape. The capsule 22 is preferably substantially impermeable to fluids in the environment as well as to ingredients contained within the osmotic pump 20 such that the migration of such materials into or out of the capsule through the impermeable material of the capsule is so low as to have substantially no adverse impact on the function of the osmotic pump 20. Materials that can be used for the capsule 22 are preferably sufficiently strong to ensure that the capsule will not leak, crack, break, or distort under stresses to which it would be subjected during implantation or under stresses due to the pressures generated during operation of the osmotic pump 20.

The capsule 22 can be formed of chemically inert and biocompatible, natural or synthetic materials that are known in the art. The capsule material is preferably a non-bioerodible material that can remain in a patient after use, such as titanium or a titanium alloy, and is largely impermeable to materials within and outside the capsule 22. However, the material of the capsule 22 can alternatively be a bioerodible material that bioerodes in the environment after dispensing the beneficial agent. Generally, preferred materials for the capsule 22 are those acceptable for human implants.

Materials suitable for construction of the capsule 22 include, but are not limited to, non-reactive polymers or biocompatible metals, alloys, or elastomers. The polymers include acrylonitrile polymers such as acrylonitrile-butadiene-styrene terpolymer, and the like; halogenated polymers such as polytetrafluoroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene, and the like. Metallic materials useful for the capsule 22 include stainless steel, titanium, platinum, tantalum, gold, and their alloys, as well as gold-plated ferrous alloys, platinum-plated ferrous alloys, cobalt-chromium alloys and titanium nitride-coated stainless steel. Elastomers useful for the capsule 22 include fluorinated or perfluorinated rubbers (e.g., Viton®). The capsule 22 can be formed from any of the above-mentioned wall-forming materials by use of a mold, with the materials applied either over the mold or inside the mold, depending on the mold configuration. Additionally, the capsule 22 can be formed by machining. Any of the wide variety of techniques known in the pharmaceutical industry can be used to form the capsule 22.

The interior of the capsule 22 receives the osmotic agent 26, which in the embodiment of the present invention depicted in FIG. 1 is an osmotic tablet. The osmotic agent 26, specifically the osmotic tablet of the embodiment of the present invention illustrated in FIG. 1, drives the osmotic flow of the osmotic pump 20. The osmotic agent 26 need not be a tablet; it may be other conceivable shapes, textures, densities, and consistencies and still be within the confines of the present invention. Additionally, more than one osmotic tablet may be used to drive the osmotic flow of the osmotic pump 20. When the osmotic pump 20 is assembled, the capsule 22 contains the osmotic agent 26.

The osmotic agent 26 is a liquid-attracting agent used to drive the flow of the beneficial agent 24 from the osmotic pump 20. The osmotic agent 26 may be an osmagent, an osmopolymer, or a mixture of the two. Species that fall within the category of osmagent, i.e., the non-volatile species which are soluble in water and create the osmotic gradient driving the osmotic inflow of water, vary widely. Examples are well known in the art and include magnesium sulfate; magnesium chloride; potassium sulfate; sodium chloride; sodium sulfate; lithium sulfate; sodium phosphate; potassium phosphate; d-mannitol; sorbitol; inositol; urea; magnesium succinate; tartaric acid; raffinose and various monosaccharides; oligosaccharides and polysaccharides, such as sucrose, glucose, lactose, fructose, and dextran; as well as mixtures of any of these various species.

Species that fall within the category of osmopolymer are hydrophilic polymers that swell upon contact with water, and these vary widely as well. Osmopolymers may be of plant or animal origin, or synthetic, and examples of osmopolymers are well known in the art. Examples include: poly(hydroxy-alkyl methacrylates) with molecular weight of 30,000 to 5,000,000; poly(vinylpyrrolidone) with molecular weight of 10,000 to 360,000; anionic and cationic hydrogels; polyelectrolyte complexes; poly(vinyl alcohol) having low acetate residual, optionally cross-linked with glyoxal, formaldehyde or glutaraldehyde and having a degree of polymerization of 200 to 30,000; a mixture of methyl cellulose, cross-linked agar and carboxymethylcellulose; a mixture of hydroxypropylmethylcellulose and sodium carboxymethylcellulose; polymers of N-vinyllactams; polyoxyethylene-polyoxypropylene gels; polyoxybutylene-polyethylene block copolymer gels; carob gum; polyacrylic gels; polyester gels; polyurea gels; polyether gels; polyamide gels; polypeptide gels; polyamino acid gels; polycellulosic gels; carbopol acidic carboxy polymers having molecular weights of 250,000 to 4,000,000; Cyanamer polyacrylamides; cross-linked indene-maleic anhydride polymers; Good-Rite polyacrylic acids having molecular weights of 80,000 to 200,000; Polyox Polyethylene oxide polymers having molecular weights of 100,000 to 5,000,000; starch graft copolymers; and Aqua-Keeps acrylate polymer polysaccharides.

The osmotic agent 26 may be manufactured by a variety of techniques, many of which are known in the art. In one such technique, an osmotically active agent is prepared as solid or semi-solid formulations and pressed into pellets or tablets whose dimensions correspond to slightly less than the internal dimensions of the respective chambers that they will occupy in the capsule interior. Depending on the nature of the materials used, the agent and other solid ingredients that may be included can be processed prior to the formation of the pellets by such procedures as ballmilling, calendaring, stirring or rollmilling to achieve a fine particle size and hence fairly uniform mixtures of each.

The beneficial agent 24 may optionally include pharmaceutically acceptable carriers and/or additional ingredients such as antioxidants, stabilizing agents, permeation enhancers, etc. In other embodiments of this invention, the beneficial agent 24 contained in the capsule 22 may include flowable compositions such as liquids, suspension, or slurries, which are typically poured into the capsule after the osmotic agent 26 and the piston 32 have been inserted in the capsule.

Patients to whom beneficial agents 24 may be administered using systems of this invention include humans and animals. The invention is of particular interest for application to humans and household, sport, and farm animals, particularly mammals. For the administration of beneficial agents, the devices of the present invention may be implanted subcutaneously or intraperitoneally, wherein aqueous body fluids or liquids are available to activate the osmotic agent 26. Devices of the invention may also be administered to the rumen of ruminant animals, in which embodiment the devices may further comprise a conventional density element for maintaining the device in the rumen for extended periods of time of up to 120 days or longer.

The present invention applies to the administration of beneficial agents in general, which include any physiologically or pharmacologically active substance. The beneficial agent 24 may be any of the agents that are known to be delivered to the body of a human or an animal such as medicaments, vitamins, nutrients, or the like.

Drug agents that may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autoacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs that may be delivered by devices according to this invention include, but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isofluorphate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-β-Estradiol, ethinyl estradiol, ethinyl estradiol 3-methyl ether, prednisolone, 17-α-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flubiprofen, fenufen, fluprofen, tolmetin, alcofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid-stimulating hormone, parathyroid and pituitary hormones, calcitonin, rennin, prolactin, corticotrophin, thyrotropic hormone, follicle-stimulating hormone, chorionic gonadotropin, gonadotropin-releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons (including alpha, beta, delta, and gamma), interleukins, growth hormones such as human growth hormone, bovine growth hormone and porcine growth hormone, fertility inhibitors such as the prostaglandins, fertility promoters, growth factors, coagulation factors, human pancreas hormone-releasing factor, analogs and derivatives of these compounds, and pharmaceutically acceptable salts of these compounds, or their analogs or derivatives.

The beneficial agent 24 can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, acetate, sulfate, laurylate, oleate, and salicylate. For acidic compounds, salts of metals, amines or organic cations may be used. Derivatives such as esters, ethers and amides can also be used. A beneficial agent can be used alone or mixed with other agents.

Osmotic pumps according to the present invention are also useful in environments outside of physiological or aqueous environments. For example, the osmotic pump may be used in intravenous systems (attached to an IV pump or bag or to an IV bottle, for example) for delivering beneficial agents to an animal or human. Osmotic pumps, according to the present invention, may also be utilized in blood oxygenators, kidney dialysis and electrophoresis, for example.

The osmotic pump 20 also includes the aforementioned semipermeable body 28, such as the semipermeable plug illustrated in FIG. 1. The semipermeable body 28 is formed of a semipermeable material that allows liquid to pass from an exterior environment of use into the capsule 22 to cause the osmotic agent 26 to swell. However, the material forming the semipermeable body 28 is largely impermeable to the materials within the capsule and other ingredients within the environment of use. As illustrated in FIG. 1, the semipermeable body 28 is in the shape of a plug that is inserted into the first opening 51 of the capsule 22 at the first end 50, closing off the first opening 51 of the capsule 22. The semipermeable body 28 may also be a membrane coating on the exterior surface of the capsule 22 or a sleeve or cap that slides over a portion of the capsule 22 to enclose the osmotic agent 26.

As shown in FIG. 1, the osmotic pump 20 includes the semipermable body 28, such as the semipermeable plug illustrated. The semipermeable body 28 is typically cylindrically shaped and has means for sealing or ribs 46 extending outwardly from the outer surface of the semipermeable body 28. The ribs 46 are the means by which the semipermeable body 28 operates like a cork or stopper, obstructing and plugging first opening 51 in the capsule 22 of the osmotic pump 20 as illustrated in FIG. 1. The means for sealing may be the exemplary ribs 46, or may be other configurations such as threads, a tight interference fit between an outer sealing surface of the plug and the capsule 22, glue, adhesives, ridges, lips, or other devices which join the semipermeable body 28 with the capsule 22 to prevent leakage. The semipermeable body 28 is, therefore, intended for at least partial insertion into an opening of the capsule 22, and the means for sealing keeps the environment of use from the inside of the capsule 22 and prevents liquid and other substances in the environment of use, besides the permeation liquid, from entering the osmotic pump 20, while also preventing materials from the inside of the delivery system from leaking or escaping to the environment of use.

The semipermeable body 28 is made from a semipermeable material. The semipermeable material of the body 28 allows liquids, especially water, to pass from an exterior environment of use into the capsule 22 to cause the osmotic agent 26 to swell. However, the semipermeable material forming the semipermeable body 28 is largely impermeable to the materials within the capsule 22 and other ingredients within the fluid environment.

Semipermeable compositions suitable for the semipermeable body 28 are well known in the art, examples of which are disclosed in U.S. Pat. No. 4,874,388, the entire disclosure of which is incorporated herein by reference. Such possible semipermeable materials from which the body 28 can be made include, but are not limited to, for example, Hytrel® polyester elastomers (DuPont), cellulose esters, cellulose ethers and cellulose ester-ethers, water flux-enhanced ethylene-vinyl acetate copolymers, semipermeable membranes made by blending a rigid polymer with water-soluble low molecular weight compounds, and other semipermeable materials well known in the art. The above cellulosic polymers have a degree of substitution ("D.S.") on the anhydroglucose unit, from greater than 0 up to 3 inclusive. By, "degree of substitution" or "D.S." is meant the average number of hydroxyl groups originally present on the anhydroglucose unit comprising the cellulose polymer that are replaced by a substituting group. Representative materials include, but are not limited to, one selected from the group consisting of cellulose acylate, cellulose diacetate, cellulose triacetate, mono-, di-, and tricellulose alkanylates, mono-, di-, and tricellulose aroylates, and the like. Exemplary cellulosic polymers include cellulose acetate having a D.S. up to 1 and an acetyl content up to 21%; cellulose acetate having a D.S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose acetate butyrate having a D.S. of 1.8, and an acetate content of 4% average weight percent and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose such as cellulose acetate butyrate and cellulose, cellulose acetate propionate, and the like.

Other materials for the semipermeable body 28 are polyurethane, polyetherblockamide (PEBAX, commercially available from ELF ATOCHEM, Inc.), injection-moldable thermoplastic polymers with some hydrophilicity such as ethylene vinyl alcohol (EVA). The composition of the semipermeable body 28 is permeable to the passage of external liquids such as water and biological liquids, and it is substantially impermeable to the passage of beneficial agents, osmopolymers, osmagents, and the like.

Figure 2:
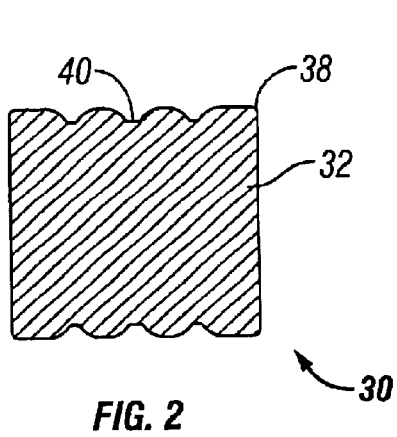
FIG. 2 is a cross-sectional view of a piston according to one embodiment of the present invention.
Figure 3:
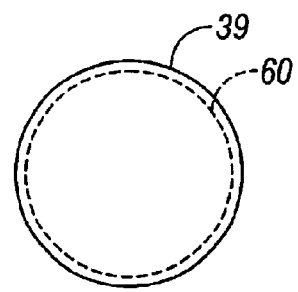
FIG. 3 is an end view of a piston according to one embodiment of the present invention.

The osmotic pump 20 also includes the movable piston 30 (shown in FIGS. 2 and 3). The piston 30 is a member that is matingly received by the hollow interior of the capsule 22 and moves when subjected to pressure from the osmotic agent 26 to displace or move the beneficial agent 24. The piston 30 forms a movable seal with the interior surface of the capsule 22. The movable seal formed by the piston 30 separates the osmotic agent 26 and the beneficial agent 24 such that the osmotic agent does not substantially leak or seep past the piston seal and adversely affect the function of the beneficial agent. Hence, the osmotic agent 26 is separated from the beneficial agent 24 by the movable piston 30.

As illustrated in FIGS. 2 and 3, the body 32 of the piston 30 is a substantially cylindrical member that is configured to fit in the capsule 22 in a sealing manner that allows the piston to slide within the capsule in the longitudinal direction of the capsule. That is, the exterior surface of the piston body 32 abuts against and slides relative to the interior cylindrical surface of the capsule 22. Because the semipermeable body 28 is lodged within the first opening 51, the piston also moves relative to the semipermeable body 28.

The piston body 32 includes annular ring-shaped protrusions or ribs 38 that define the movable or sliding seal with the inner surface of the capsule 22. The ribs 38 are the most outwardly radial surface of the piston body 32. The ribs 38 are the means by which the piston 30 forms a seal with the interior surface of the capsule 22. Thus, the outermost radial diameter 39 of the piston body 32 illustrated in FIGS. 2 and 3 includes four ribs; other pistons, according to the present invention, may include one, two, three, or more ribs. Additionally, the piston body 32 need not include ribs. For example, the exterior surface of the piston body can be entirely cylindrical such that the entire cylindrical exterior surface of the piston body affects a seal with the interior surface of the capsule 22. However, ribs 38 are preferred as they effect a better movable seal with the interior surface of the capsule 22, as compared to a piston body having an exterior surface that is entirely cylindrical.

The number and size of ribs 38 on the piston body 32 are determined by the amount of friction and the redundancy of seals desired in the piston 30. A cylindrical piston without ribs would increase the amount of friction between the piston 30 and the interior surface of the capsule 22. A large amount of friction between the piston 30 and the interior surface of the capsule 22 could lead to increases in start-up delay in order for the piston to overcome the friction with the interior surface of the capsule. The friction between the piston 30 and the interior surface of the capsule 22 could also lead to pulsatile delivery of beneficial agent 24 from the device or to a slip/stick type of movement of the piston 30. If zero-order release of beneficial agent 24 is desired, then pulsatile or slip-stick movement of the piston is unacceptable. The number of ribs 38 included on the piston body 32 is selected to provide a suitable seal between the osmotic agent 26 and the beneficial agent 24 during storage and operation of the osmotic pump 20, while maintaining the magnitude of friction generated between the piston 32 and the interior surface of the capsule 22 at a level that allows delivery of the beneficial agent 24 at a desired rate or rate profile.

The size and shape of the ribs 38 on the piston body 32 also play a role in the way the piston 30 moves in the capsule 22, and the amount of sealing provided by the piston 30. As the diameter 39 of the piston core 60 is increased, the depth of valleys 40 or areas between the ribs 38 decrease. As the valleys 40 are truncated, the space available for air to be entrapped during the process of inserting the piston 30 into the capsule 22 is reduced. Because air is compressible, air in the capsule 22 must be compressed before the beneficial agent 24 can begin to be delivered from the capsule 22. Therefore, the less air that is entrapped between the ribs 38 of the piston body 32, the shorter the start-up time.

Truncation of the valleys 40 between the ribs 38 of a piston 30 of the present invention also works to reduce the springiness and the linear compressibility of the piston 30. A reduction in the compressibility reduces the start-up time for delivery of beneficial agent 24.

Where it is desired to provide an osmotic pump 20 with a coated piston 30, truncation of the valleys 40 between the ribs 38 of the piston body 32 also makes the piston 30 easier to coat. Coating of the piston 30 may include, but is not limited to, coating done by known liquid-immersion and spray-coating processes. As the depth of the valleys 40 formed between ribs 38 included on a piston 30 increases, the likelihood of an incomplete or non-uniform coating also increases. In particular, as the depth of the valleys 40 formed between ribs 38 increases, the likelihood that the sides and bottom of the valley 40 will not be coated due to shadowing or obstruction by adjacent ribs 38 also increases. In addition, as the depth of the valleys formed between the ribs increases, the likelihood that a bubble of air will become entrapped therein during a coating process also increases. Therefore, truncation of the valleys 40 formed between ribs 38 included on a piston 30 of the present invention eases the task of providing the piston 30 with a uniform coating, where desired.

The piston 30 in the present invention is designed to maximize the beneficial agent 24 and/or osmotic agent 26 payload. This means that the piston 30 of the present invention was reduced in size to allow for more beneficial agent 24 and/or osmotic agent 26 capacity without increasing the size of the capsule 22. The piston 30 of the present invention is reduced in size, exhibiting a length-to-total-width ratio of about 1.1:1 without any increases in leakage past the piston 30 or change in zero-order delivery of the beneficial agent 24. Moreover, to reduce the possibility of air entrapment around the ribs 38 of the piston, body 32, the ribs 38 of the piston body 32 of the present invention are also reduced in size. In particular, the piston 30 of the present invention has a core-diameter-to-total-diameter ratio of about 0.9:1.

In one embodiment of the present invention, the 30 piston has a length of 6.00 millimeters (0.237 inches) and a total diameter of 5.50 millimeters (0.217 inches), giving a length-to-total-diameter ratio of 1.1:1. The piston 30 in this embodiment also has a core diameter 39 of 4.90 millimeters (0.193 inches), giving a core-diameter-to-total-diameter ratio of 0.89:1.

The piston body 32 is preferably formed of an impermeable resilient and inert material. In general, materials suitable for the piston body 32 are elastomeric materials including the non-reactive polymers listed above in reference to the materials for capsule 22, as well as elastomers in general, such as polyurethanes and polyamides, chlorinated rubbers, fluorinated rubbers (such as Viton®), styrene-butadiene rubbers, and chloroprene rubbers.

The piston body 32 is preferably injection molded. However, the piston body 32 may be fashioned by a different process. For example, the piston body 32 may also be made from extrusion, reaction injection molding, rotational molding, thermoforming, compression molding, and other known processes.

It is preferable that the piston body 32 be substantially impervious to liquids, such that the osmotic agent 26 and the liquid that permeates through the semipermeable body 28 does not diffuse through the piston body 32 and affect the beneficial agent 24 located on the side of the piston 30 opposite from that of the osmotic agent 26, and such that the beneficial agent 24 does not diffuse through the piston body 32 and affect the performance of the osmotic agent 26.

While the invention has been described in detail with reference to a preferred embodiment thereof, it will be apparent to one skilled in the art that various changes can be made and equivalents employed without departing from the spirit and scope of the invention.

I claim:

1. An osmotic delivery system comprising:
   a capsule, said capsule having an interior for holding a beneficial agent, said interior having an interior surface;
   an osmotic agent located in said interior;
   a semipermeable body in liquid communication with said capsule for permitting liquid to permeate through said semipermeable body to said osmotic agent; and
   a piston having a length to total diameter ratio of about 1.1:1 and a core-diameter-to-overall-diameter ratio of about 0.9:1 located within said interior of said capsule, being movable with respect to said interior surface of said capsule, defining a movable seal with said interior surface of said capsule that separates said osmotic agent from said beneficial agent;
   said osmotic agent located between said piston and said semipermeable body, said osmotic agent for imbibing fluid from a surrounding environment through said semipermeable body to cause said piston to move and, in turn, cause delivery of said beneficial agent from said capsule.

2. The osmotic delivery system according to claim 1, wherein said piston includes one or a plurality of ribs for effecting said movable seal with said interior surface.

3. The osmotic delivery system according to claim 1, wherein said capsule includes a cylindrical tube.

4. The osmotic delivery system according to claim 3, wherein said cylindrical tube includes an opening and said semipermeable body includes a semipermeable plug, said semipermeable plug located within said opening.

5. The osmotic delivery system according to claim 1, wherein said osmotic agent includes a tablet.

6. An osmotic delivery system comprising:
a piston having a length-to-overall-diameter ratio of about 1.1:1 and a core-diameter-to-overall-diameter ratio of about 0.9:1;
an osmotic agent; and
an enclosure having an interior holding said piston and said osmotic agent, said piston being movable with respect to said enclosure, and said enclosure having a semipermeable body in liquid communication with said osmotic agent for permitting liquid to permeate through said semipermeable body to said osmotic agent, said osmotic agent for imbibing fluid from a surrounding environment and causing said piston to move.

7. The osmotic delivery system according to claim 6, wherein said interior of said enclosure includes an interior surface, said piston abutting against said interior surface.

8. The osmotic delivery system according to claim 6, wherein said semipermeable body is located within said interior of said enclosure.

9. The osmotic delivery system according to claim 6, wherein said enclosure is fluid impermeable.

10. The osmotic delivery system according to claim 6, wherein said osmotic agent is located between said semipermeable body and said piston.

11. The osmotic delivery system according to claim 6, further comprising a beneficial agent located in said interior of said enclosure, said beneficial agent being delivered from said enclosure when said piston moves.

12. The osmotic delivery system according to claim 6, wherein said piston is fluid impermeable.

13. The osmotic delivery system according to claim 6, wherein said piston includes at least one rib for effecting a movable seal with said enclosure.

14. The osmotic delivery system according to claim 6, further comprising a beneficial agent located in said interior of said enclosure, said piston defining a movable seal that separates said osmotic agent from said beneficial agent.

15. An osmotic delivery system comprising:
a capsule having a tubular interior, said tubular interior having an interior surface;
a semipermeable body located at least partially within said tubular interior;
an osmotic agent located between said semipermeable body and a piston;
a beneficial agent located within said tubular interior; and
said piston located within said tubular interior, said piston having a length-to-overall-diameter ratio of about 1.1:1 and a core-diameter-to-overall-diameter ratio of about 0.9:1, said piston separating said beneficial agent from said osmotic agent, and being movable with respect to said interior surface of said tubular interior and with respect to said semipermeable body.

16. The osmotic delivery system according to claim 15, wherein said piston includes at least one rib.

* * * * *